US009895286B2

(12) United States Patent

Rydel

(10) Patent No.: US 9,895,286 B2
(45) Date of Patent: Feb. 20, 2018

(54) RADIALLY ADJUSTABLE SEX TOY

(71) Applicant: Allison Alayne Rydel, Woodbury, MN (US)

(72) Inventor: Allison Alayne Rydel, Woodbury, MN (US)

( * ) Notice: Subject to any disclaimer, the term of this patent is extended or adjusted under 35 U.S.C. 154(b) by 113 days.

(21) Appl. No.: 15/198,724

(22) Filed: Jun. 30, 2016

(65) Prior Publication Data

US 2017/0020775 A1 Jan. 26, 2017

Related U.S. Application Data

(60) Provisional application No. 62/195,097, filed on Jul. 21, 2015.

(51) Int. Cl.

| | |
|---|---|
| ***A61F 5/00*** | (2006.01) |
| ***A61H 19/00*** | (2006.01) |
| *A61H 23/02* | (2006.01) |

(52) U.S. Cl.

CPC ....... *A61H 19/44* (2013.01); *A61H 2023/029* (2013.01); *A61H 2201/0153* (2013.01); *A61H 2201/0192* (2013.01); *A61H 2201/1253* (2013.01); *A61H 2201/1436* (2013.01); *A61H 2201/1676* (2013.01); *A61H 2201/5007* (2013.01)

(58) Field of Classification Search

CPC ........ A61H 19/00; A61H 19/34; A61H 19/40; A61H 19/44; A61H 21/00; A61H 23/00

USPC ........................................ 600/38–41; 601/46

See application file for complete search history.

(56) References Cited

U.S. PATENT DOCUMENTS 7,828,717 B2 * 11/2010 Lee ........................ A61H 19/34 600/38
8,308,631 B2 * 11/2012 Kobashikawa ........ A61H 19/34 600/38
9,066,843 B1 * 6/2015 Greco .................... A61H 19/44

* cited by examiner

*Primary Examiner* — John Lacyk

(57) ABSTRACT

A dildo with adjustable girth is provided through a construction including a base, dilating mechanisms, and an elastic membrane which is fit over the dilating mechanisms. The dilating mechanisms are formed from a shaft, lateral bracing supports, and a drive mechanism. The lateral bracing supports are connected along the shaft, forming an inner structure for the elastic membrane. The drive mechanism, when activated, causes the shaft to rotate, which in turn causes the lateral bracing supports to press against and expand the elastic membrane. Preferably, two dilating mechanisms are provided in order to evenly expand the dildo to each side. The drive mechanisms can be either electrically operated (for example a corded input or an internal battery powering a motor) or manually operated (for example a user manually turning a handle to rotate the shaft). An articulated shaft can also be added to allow for bending of the dildo.

9 Claims, 15 Drawing Sheets

RADIALLY ADJUSTABLE SEX TOY

The current application claims a priority to the U.S. Provisional Patent application serial number 62/195,097 filed on Jul. 21, 2015.

FIELD OF THE INVENTION

The present invention relates generally to a radially adjustable sex toy, which used rotating structural supports to switch between a contracted configuration and an expanded configuration.

BACKGROUND OF THE INVENTION

Sex toys are popular with many people to enhance sexual experiences. Many sex toys are provided for use individually or with one or more partners. There exist a wide range of applications for sex toys; for example, many people utilize specialized outfits, paddles, or dildos. The present invention addresses the latter example, seeking to provide an improved dildo. Dildos are commonly used for insertion into an orifice, most commonly the vaginal cavity or anal cavity. Dildos are currently provided with a variety of features to enhance the user experience. One such feature is the ability to adjust the dimensions (e.g. "girth") of the dildo. The present invention seeks to provide an improved means to accomplish this, utilizing a rotating system that effectively contracts or expands the dildo.

DETAIL DESCRIPTIONS OF THE INVENTION

Figure 1:
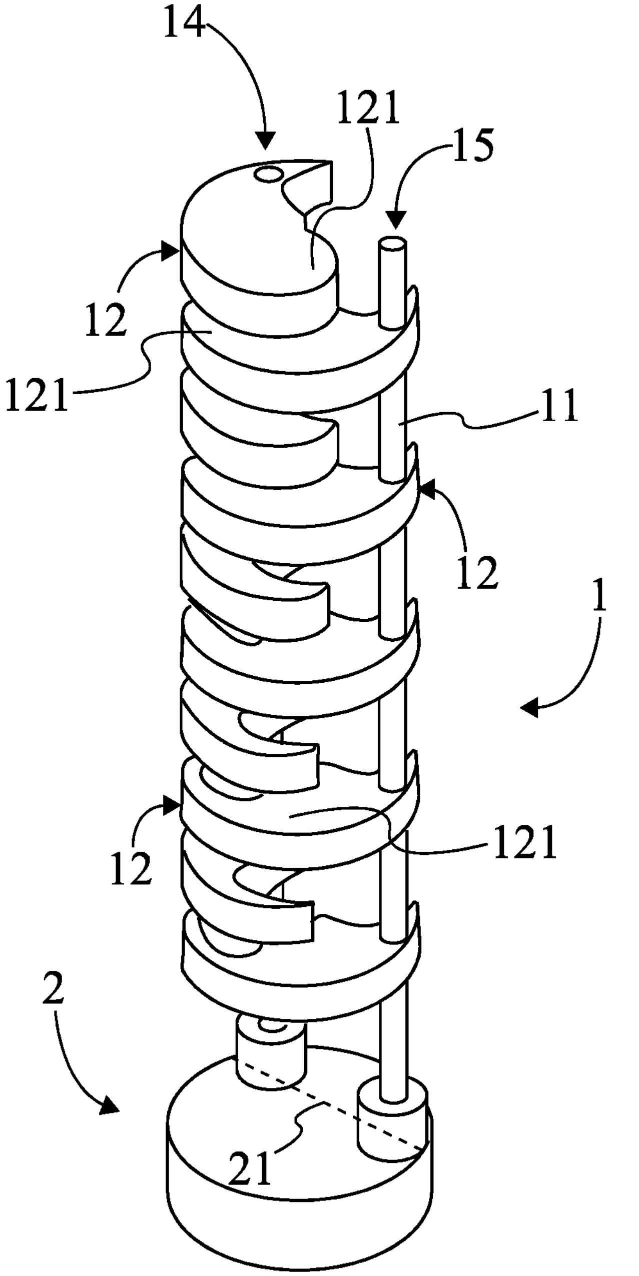
FIG. 1 is a perspective view showing a core embodiment of the present invention in a contracted configuration.
Figure 2:
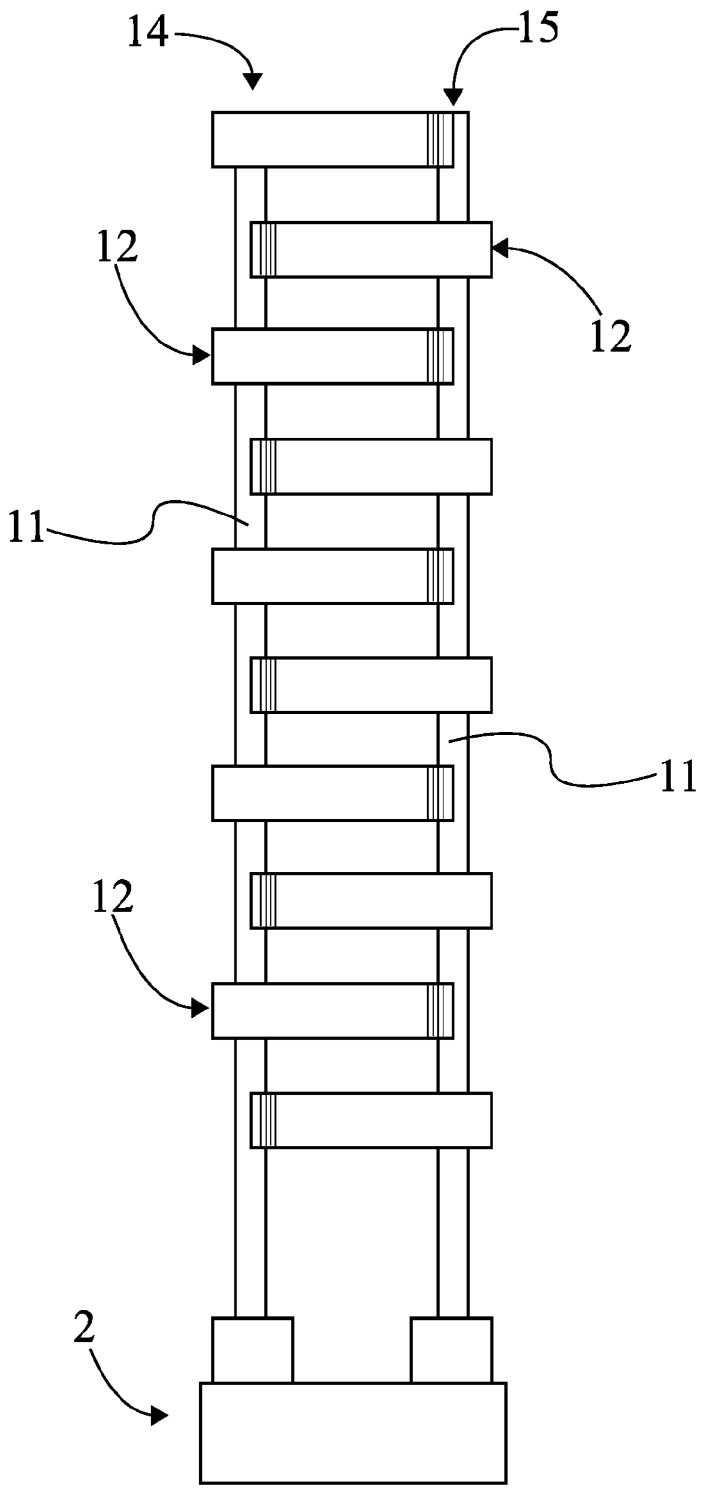
FIG. 2 is a front view showing the core embodiment of the present invention in the contracted configuration.

All illustrations of the drawings are for the purpose of describing selected versions of the present invention and are not intended to limit the scope of the present invention.

The present invention is a radially adjustable sex toy which allows a user to increase and decrease the effective radius. Though the present invention is intended for sexual applications, it ultimately may be utilized in any manner and for any purpose as desired by a user. Described at a core level, the present invention comprises a plurality of dilating mechanisms 1, a base 2, and an elastic membrane 3. Each of the dilating mechanisms 1 can be engaged in order to switch the present invention from a contracted configuration to an expanded configuration, which effectively allows for different girths to be selected. The base 2 serves as a mount for the dilating mechanisms 1. The elastic membrane 3 encloses the dilating mechanisms 1 in order to provide a profile which is both phallic and comfortable; the elastic membrane 3 thus increase ergonomics of the present invention, especially as related to for example vaginal insertion or anal insertion. In short, the elastic membrane 3 serves as a skin for the present invention, with the elastic membrane 3 expanding and contracting in correlation to actuation of the plurality of dilating mechanisms 1. This basic configuration of components is subsequently elaborated upon. The present invention, including potential embodiments, is illustrated via FIG. 1-FIG. 15.

Each dilating mechanism 1 comprises a primary shaft 11, and a plurality of lateral bracing members 12. A drive mechanism 13 is provided to enable operation of the dilating mechanisms 1. Potentially, the drive mechanism 13 can be divided into sub-units, with a sub-unit being provided for each of the plurality of dilating mechanisms 1. Also possible is a single drive mechanism 13 which is able to operate each of the plurality of dilating mechanisms 1, for example by means of a gearbox that couples the drive mechanism 13 to the each of the plurality of dilating mechanisms 1. The primary shaft 11 is rotatably connected into the base 2, traversing into the base at a ninety degree angle. Additional, it is preferable that the primary shafts 11 of the plurality of dilating mechanisms 1 are peripherally distributed around the base. This allows for larger sizes of lateral bracing members 12 than an embodiment where the primary shafts 11 are positioned near the center of the base 2. Resultantly, the preferred peripherally-aligned primary shafts 11 are implemented to obtain a more efficient layout. This allows for optimized size of the plurality of lateral bracing members 12. The drive mechanism 13 is provided to drive rotation of the primary shaft 11 through an appropriate coupling.

Figure 3:
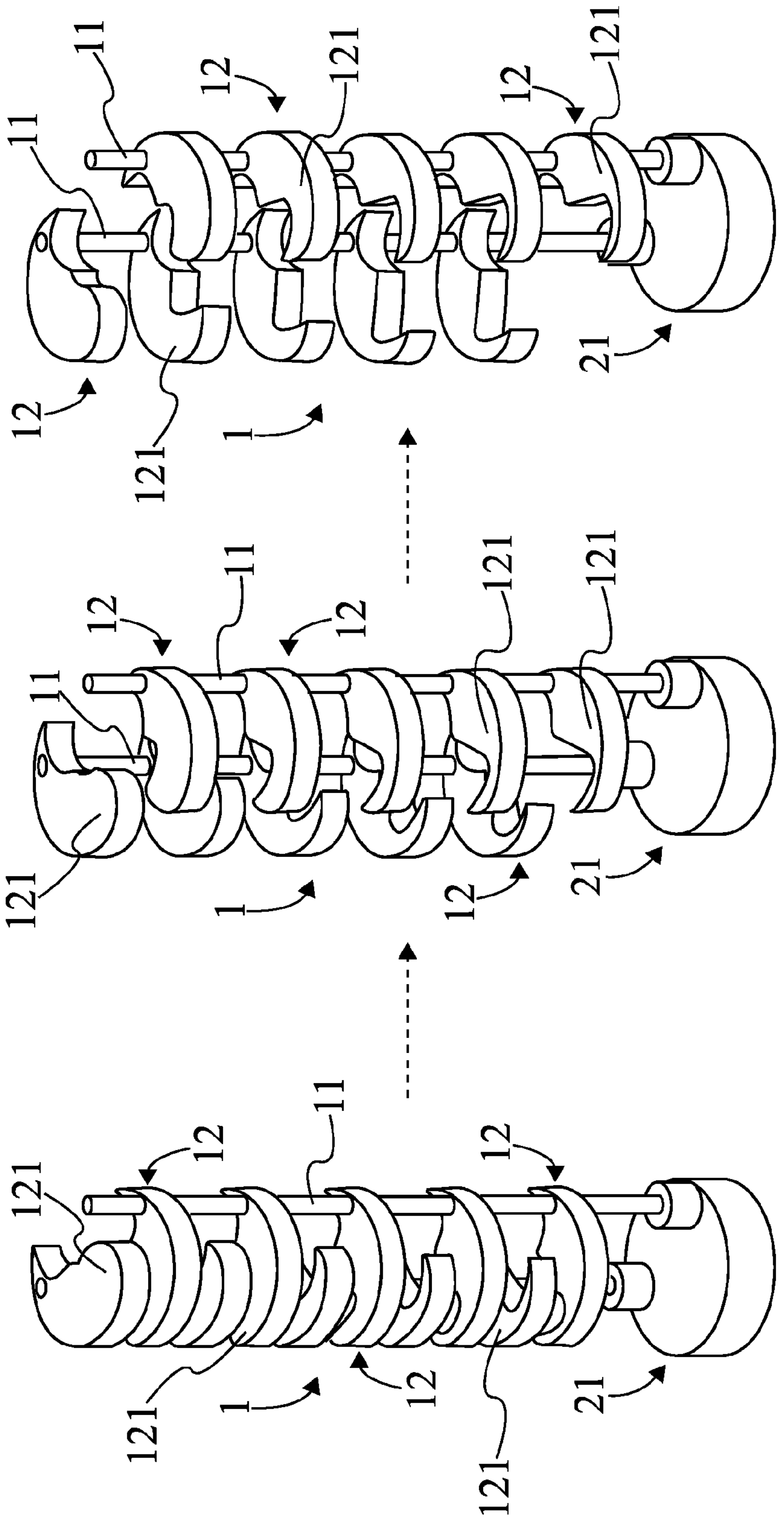
FIG. 3 is a perspective view showing the core embodiment of the present invention transitioning from the contracted configuration to an expanded configuration.
Figure 4:
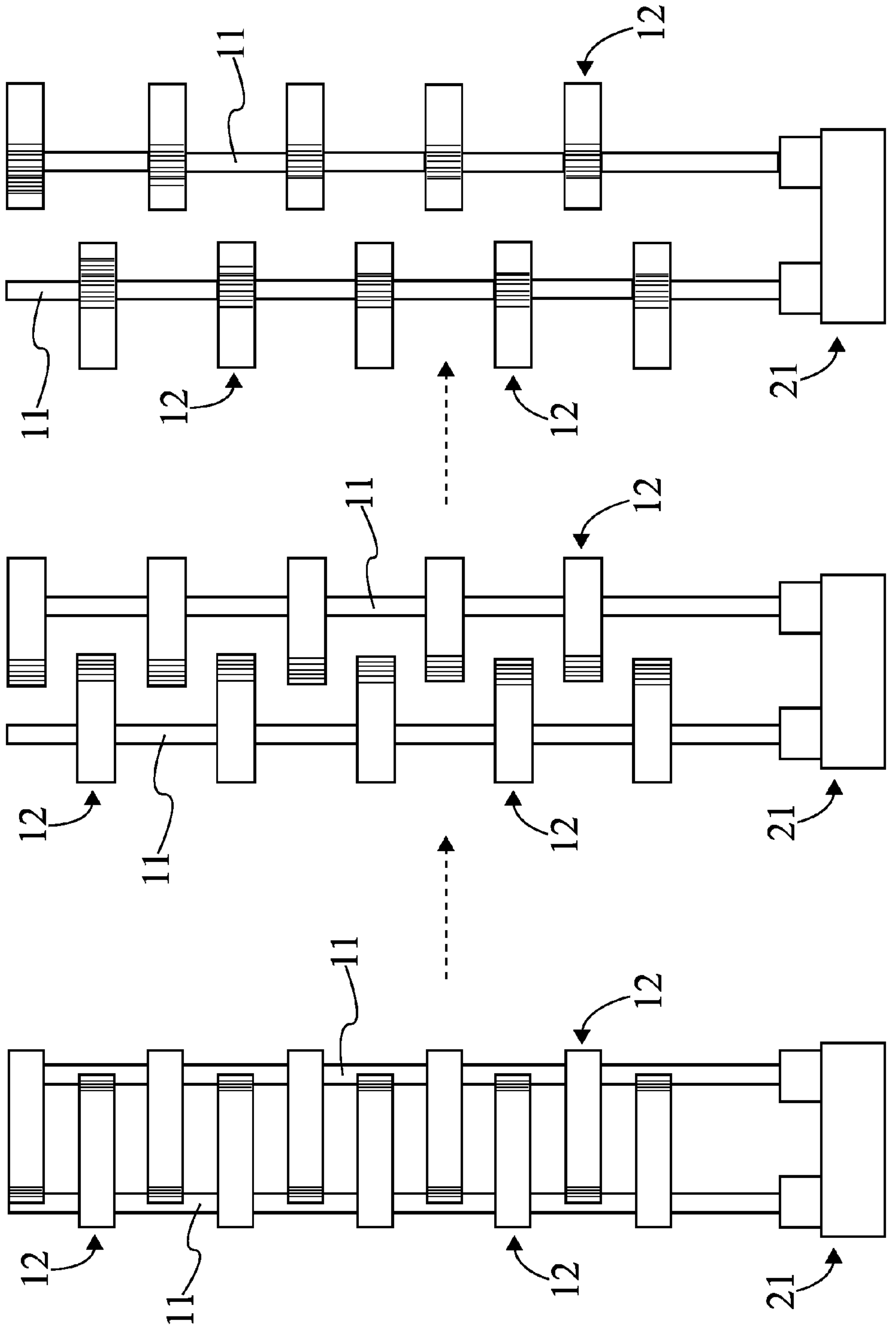
FIG. 4 is a front view showing the core embodiment of the present invention transitioning from the contracted configuration to the expanded configuration.
Figure 5:
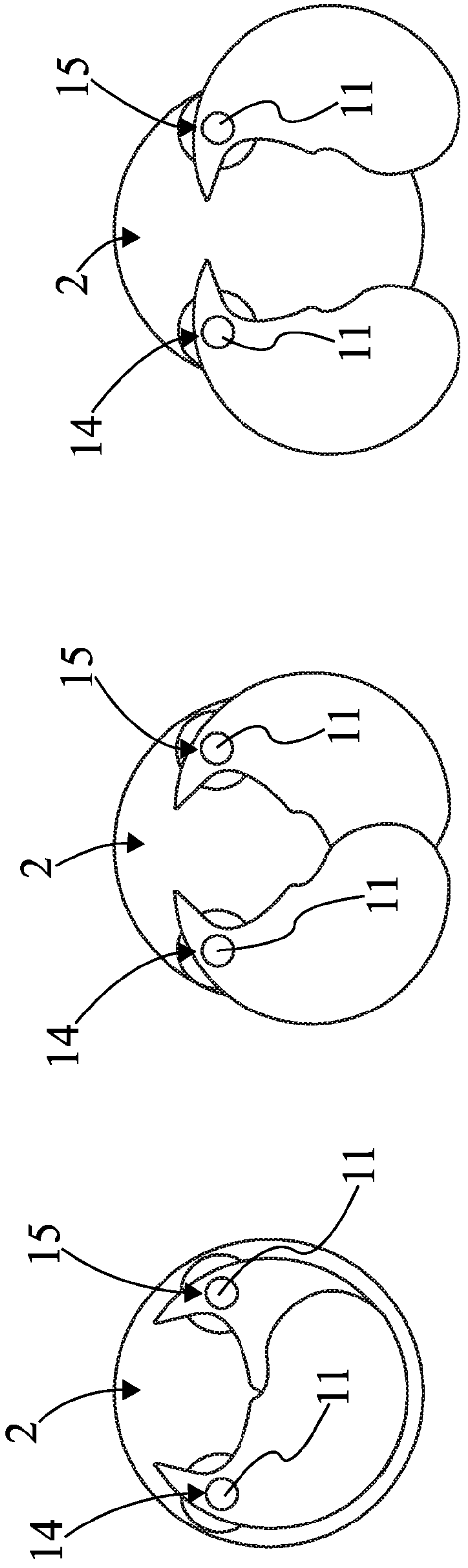
FIG. 5 is a top view showing the core embodiment of the present invention transitioning from the contracted configuration to the expanded configuration.
Figure 6:
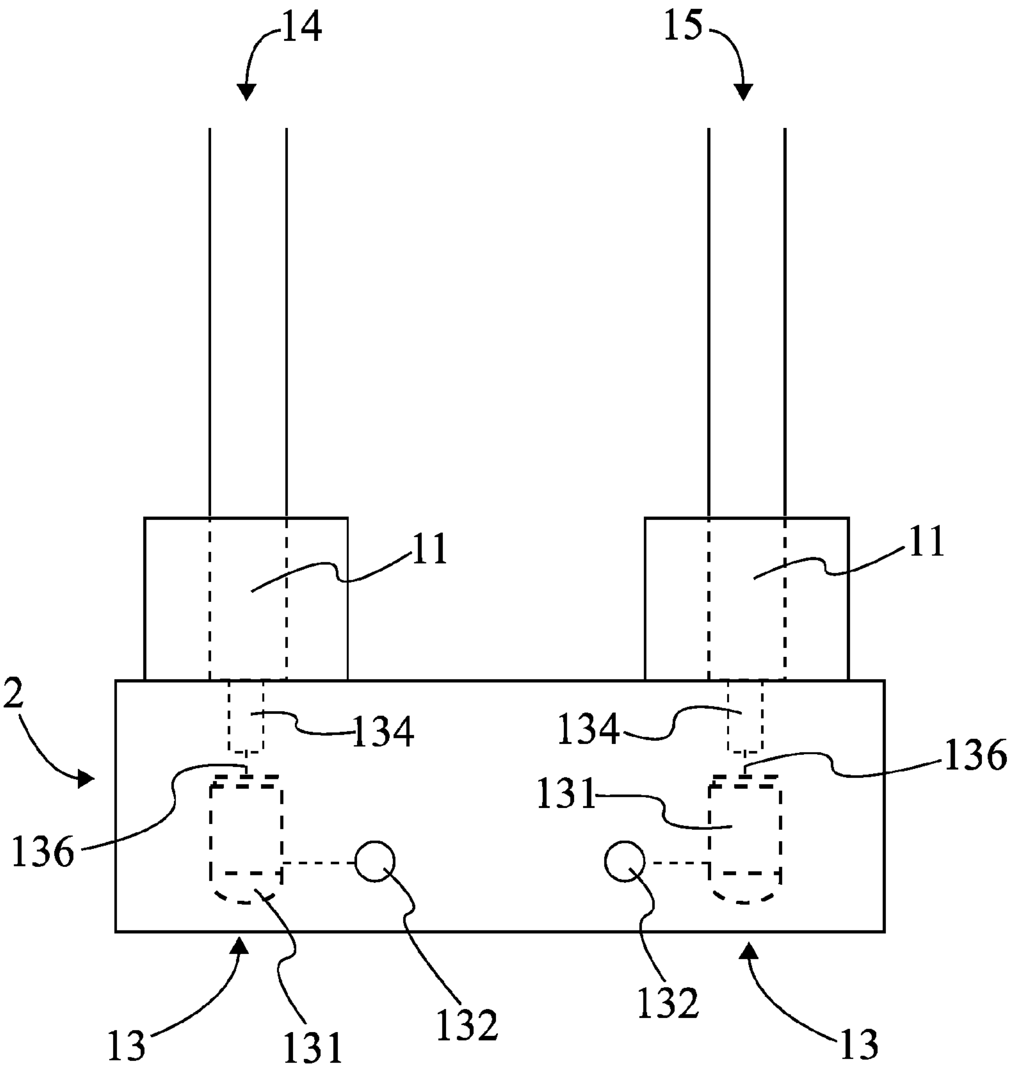
FIG. 6 is an enhanced front view showing a potential embodiment for a drive mechanism utilizing an external electrical input.
Figure 7:
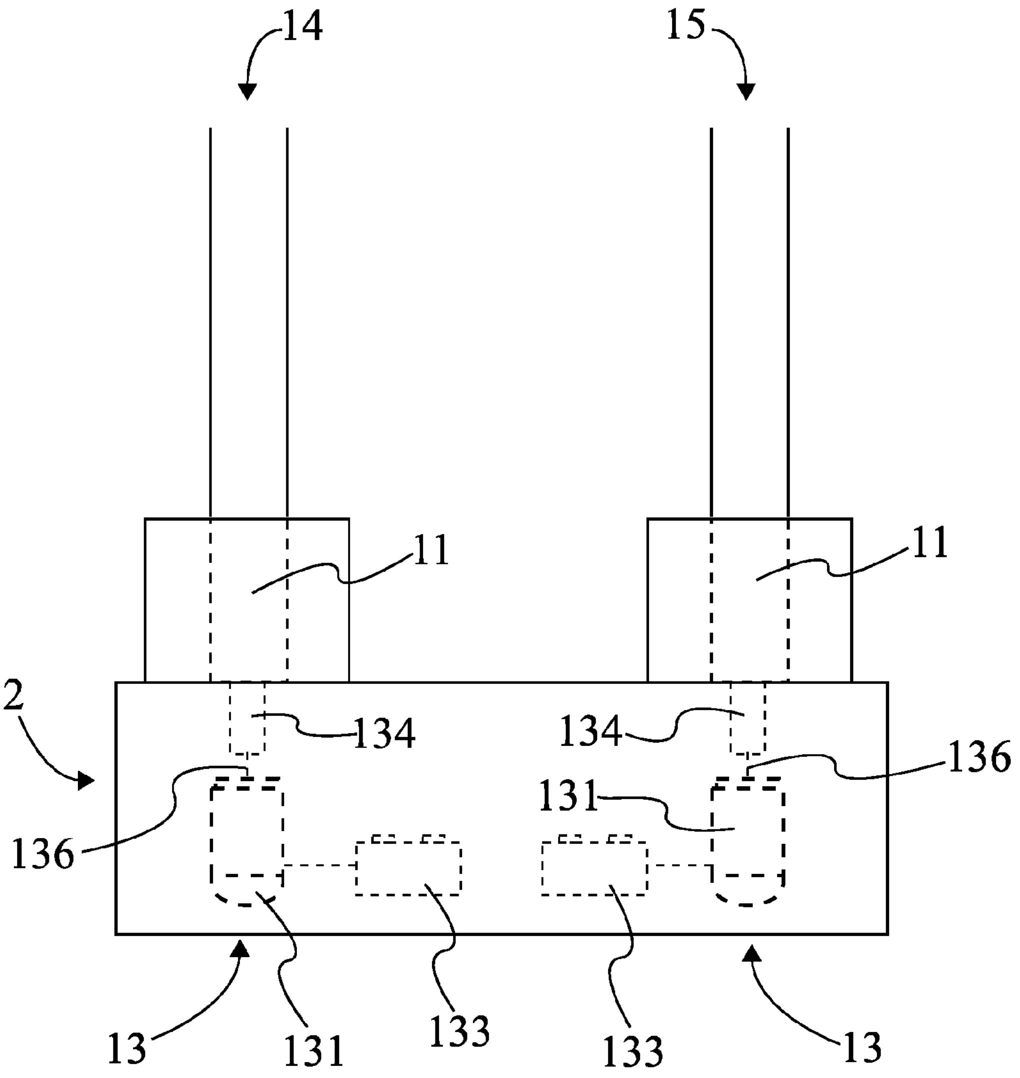
FIG. 7 is an enhanced front view showing a potential embodiment for a drive mechanism utilizing an internal electrical source.

Describing the lateral bracing members 12 in more detail, each of the plurality of lateral bracing members 12 is connected adjacent and perpendicular to the primary shaft 11. Thus, each bracing member 12 is radially extended from the primary shaft 11 in a manner similar to a cam. The plurality of lateral bracing members 12 is distributed along the primary shaft 11, with the collected lateral bracing members 12 forming a linear arrangement that is used to support the elastic membrane 3 in a generally cylindrical shape. The plurality of lateral bracing members 12 is able to give shape to the elastic membrane 3 as the plurality of lateral bracing members 12, along with the primary shaft 11, is sleeved by the elastic membrane 3. The drive mechanism 13 itself is housed in the base, where the primary shaft 11 of each of the plurality of dilating mechanisms 1 is torsionally coupled with said drive mechanism 13. Through this coupling, the drive mechanism 13 is able to impart rotation to the primary shaft 11. The rotation results in the plurality of lateral bracing members 12 turning outwards (i.e. switching the present invention to an expanded configuration) or turning inwards (i.e. switching the present invention to a contracted configuration). In this manner a user can adjust the girth (radius) of the present invention as desired. FIG. 3-FIG. 5 provide visual examples of this radial adjustment.

As the present invention is intended to be phallic in nature, in the preferred embodiment the base 2 is an ellipsoid, having a rounded shape. Even more ideally, the base 2 is circularly shaped (a circle being a subset of an ellipse), but ultimately any ellipsoid or similarly rounded shape is suitable. To match this general shape, each of the plurality of lateral bracing members 12 comprises a lobe 121. The lobe 121 is perimetrically aligned with the base 2, such that in a contracted configuration the outside edge of the lobe 121 remains within a profile of the base 2; only in an open position does the lobe 121 extend beyond the boundary of the base 2. The combination of an elliptical base 2 and lobes 121 allow for the present invention to maintain a comfortable cylindrical shape in both the contracted configuration and the expanded configuration. The core configuration as heretofore described is illustrated in the contracted configuration via FIG. 1 and FIG. 2.

For optimized adjustment of the present invention, the plurality of dilating mechanisms 1 comprises a first dilating mechanism 14 and a second dilating mechanism 15. The first dilating mechanism 14 and the second dilating mechanism 15 are positioned opposite each other across the base 2, preferably on a line that connects two points of the perimeter of the base 2. This is known as a chord 21 in geometry terms. Regarding the lateral bracing members 12, the plurality of lateral bracing members 12 of the first dilating mechanism 14 is axially offset from the plurality of lateral bracing members 12 of the second dilating mechanism 15. In other words, each plurality of lateral bracing members 12 rotates about a different axis. The axis of rotation for each plurality of lateral bracing members 12 is simply its corresponding primary shaft 11. The relative position of the two dilating mechanisms 1 is visualized in FIG. 1-FIG. 5.

Additionally, the plurality of lateral bracing members 12 of the first dilating mechanism 14 is interspersed with the plurality of lateral bracing members 12 of the second dilating mechanism 15. Thus, each of the lateral bracing members 12 from the first dilating mechanism 14 are alternately positioned with the lateral bracing members 12 from the second dilating mechanism 15 along a vertical axis. Such a configuration is necessary when multiple dilating mechanisms 1 are provided, as it allows for larger sized lobes 121 to be used. For example, if one of the lateral bracing members 12 of the first dilating mechanism 14 shared a plane with one of the lateral bracing members 15 of the second dilating mechanism 15, they could be no larger than half the area of the base. By ensuring that each lateral bracing member 12 is on a plane that is not shared with any of the other lateral bracing members 12, the maximum potential size of the lobe 121 is increased. The alternative positioning of the plurality of lateral bracing members 12 is shown in FIG. 1-FIG. 4.

The drive mechanism 13 of the present invention can be implemented in one of three primary variations. One of these is an electrical cord-powered variation. In this example the drive mechanism 13 comprises at least one motor 131 and a power input 132. The at least one motor 131 is housed in the base 2, where it is able to mechanically rotate the primary shaft 11 of the dilating mechanism 1 when supplied with a requisite amount of electricity. The power input 132 traverses into the base 2, where it is electrically connected with the motor 131. Resultantly, an external supply of power can be hooked up to the present invention via the power input 132, for example by means of a power cable. This example embodiment is depicted through FIG. 6.

In another of the variations, the drive mechanism comprises at least one motor 131 and a battery 133. As with the previous example, the at least one motor 131 is housed in the base 2 and operatively coupled to the primary shaft 11 of the dilating mechanism 1. Thus, when the motor 131 is activated it drives rotation of the primary shaft 11. The battery 133 is also housed in the base 2 in order to be both hidden as well as proximal to the motor 131. The battery 133 is electrically connected to the motor 131, providing the energy necessary for operation of the motor 131 and resultant rotation of the primary shaft 11 of the dilating mechanism 1. This example embodiment is depicted through FIG. 7. The primary difference between this configuration of drive mechanism 13 and the previous configuration (i.e. with power input 132) is that the power source is internal (i.e. the battery) in this example compared to being external (i.e. the power cord connected to an outlet or similar source) in the previous example.

In the aforementioned embodiments (i.e. with power input 132 and with battery 133), multiple motors 131 can be used (as shown in the corresponding FIG. 6 and FIG. 7), with each motor 131 engaging a separate primary shaft 11. Alternatively, as earlier referenced a single motor 131 can be coupled with a gearbox, the gearbox in turn operating the primary shafts 11 of both the first dilating mechanism 14 and the second dilating mechanism 15. This configuration negates the need for multiple motors 131. In both these motorized variations, an output 136 of the motor 131 is torsionally coupled to the primary shaft 11. This output 136 links the motor 131 and the primary shaft 11, with rotation of the former being used to drive rotation of the latter. An electrical source the allows non-human power to be used for the present invention.

In both of these variations, it is preferable to provide a motor-controlling interface, preferably positioned on the base 2 so as to be unobtrusive. The motor-controlling interface, for example, might comprise an on/off switch and a directionality switch. The on/off switch is integrated into a power circuit that connects the power input 132 or battery 133 with the motor 131; as a result, closing or opening the switch completes or breaks the circuit. In this manner, the motor 131 can be engaged (when the switch is closed to complete the circuit) or disengaged (when the switch is opened to break the circuit).

In the third variation, the drive mechanism 13 comprises at least one crankshaft 134 and at least one handle 135. The at least one crankshaft 134 is extruded from the base 2, serving to effectively connect the at least one handle 135 to the primary shaft 11. The at least one handle 135 is positioned adjacent to the base 2 in order to allow the at least one handle 135 to be rotated relative to the base 2. Thanks to the connection of the at least one handle 135 to the primary shaft 11 by means of the at least one crankshaft 134, this rotation causes the primary shaft 11 to rotate by an equal amount.

Figure 8:
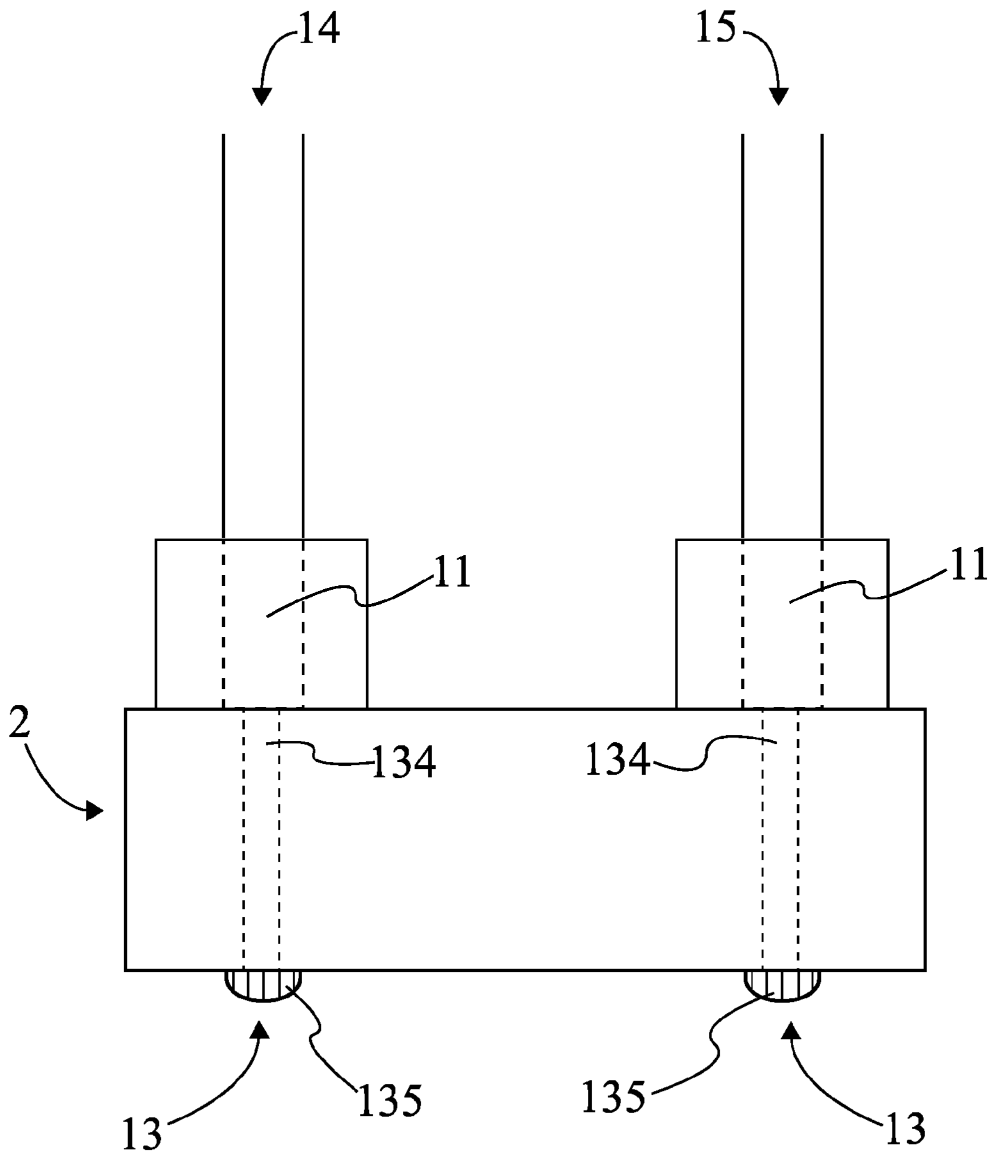
FIG. 8 is an enhanced front view showing a potential embodiment for a drive mechanism utilizing a human powered handle and crankshaft.
Figure 9:
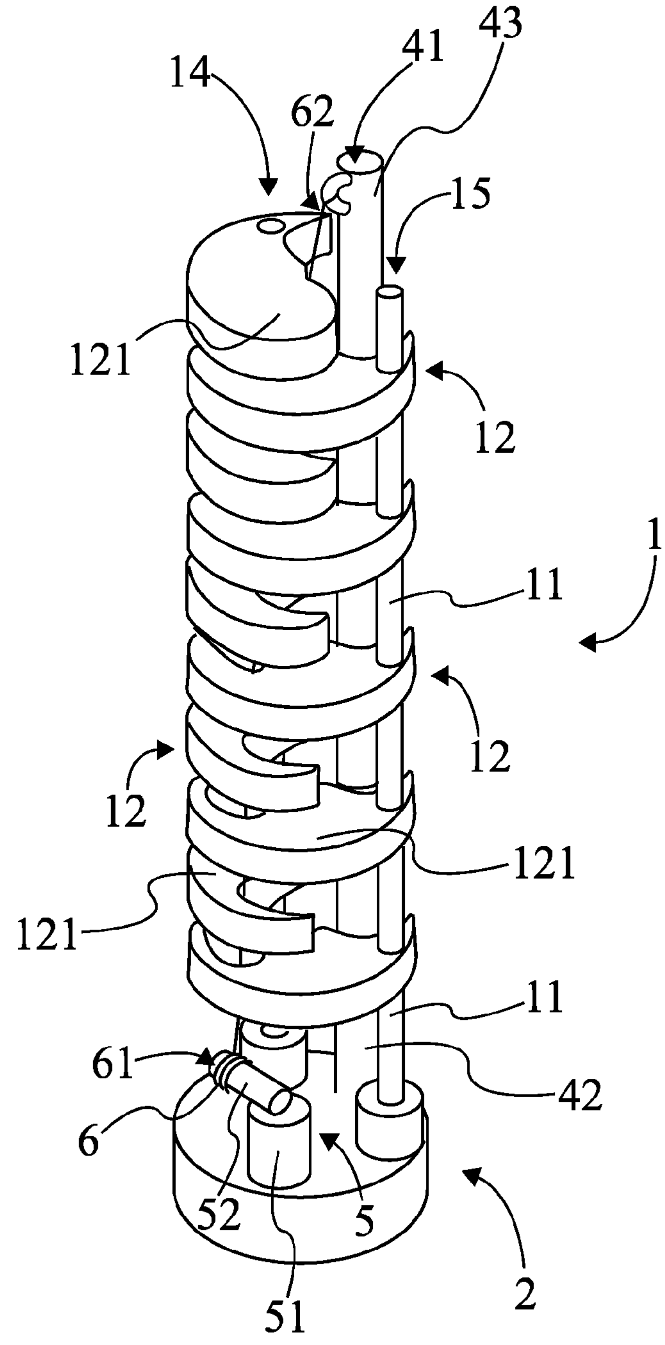
FIG. 9 is a perspective view showing a bendable embodiment of the present invention in a contracted configuration.
Figure 10:
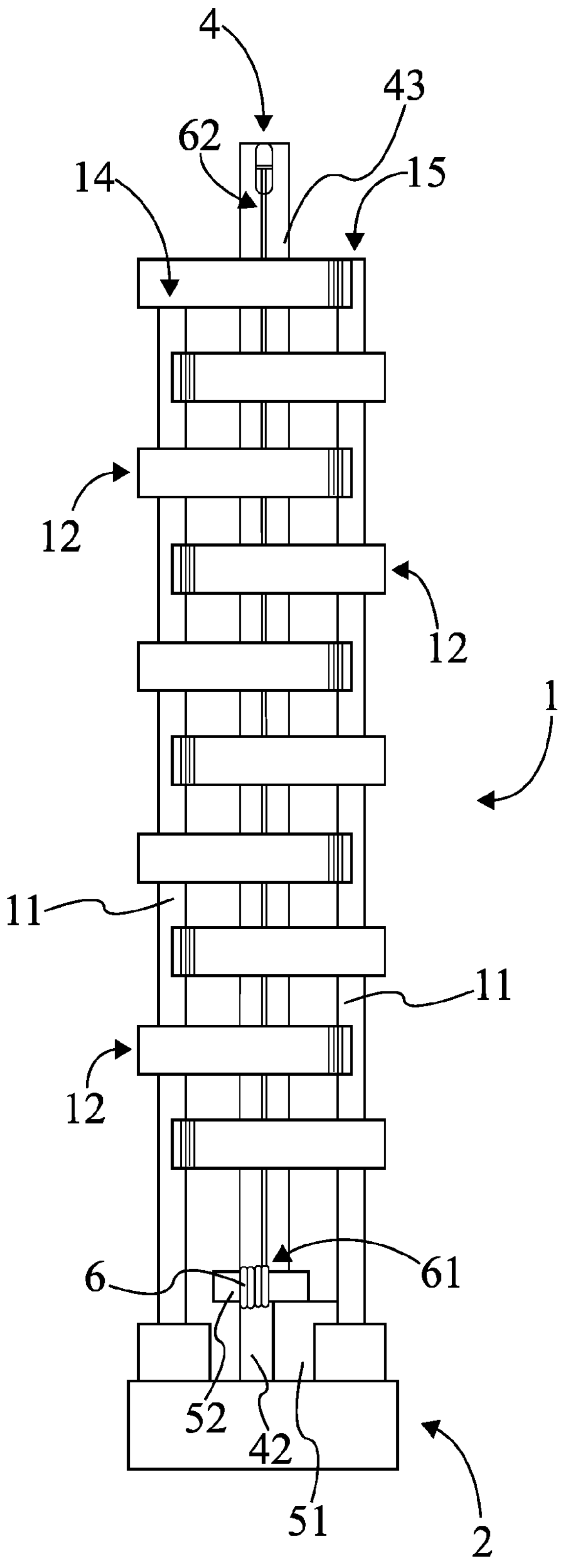
FIG. 10 is a front view showing the bendable embodiment of the present invention in the contracted configuration.

The at least one handle 135 thus provides a compact and easily operated interface that allows a person to manually rotate the primary shaft 11 to open and close the plurality of lateral bracing members 12. This example embodiment is depicted in FIG. 8.

As with the first two variations, this third variation can utilize a single handle 135 or provide a corresponding handle 135 for each primary shaft 11. If a single handle 135 is utilized, it is coupled to a crankshaft 134 for each primary shaft 11 through a gearbox, allowing the single handle 135 to operate both the first dilating mechanism 14 and the second dilating mechanism 15. Alternatively, multiple handles 135 can be provided, with each handle 135 being coupled to a corresponding primary shaft 11 by means of a connecting crankshaft 134. This alternative configuration is illustrated in the corresponding FIG. 8.

Reiterating the above, variations of the drive mechanism 13 allow for a motorized implementation or a human powered implementation. The motorized implantation is compatible with both external power sources (e.g. via power cord) and internal power sources (e.g. a battery 133). The key result, regardless of specific implementation, is the ability to impart rotation to the primary shaft 11 in order to open and close the plurality of lateral bracing members 12.

Changes can be made to the example variations while remaining within the scope of the present invention. For example, as mentioned the drive mechanism 13 can be divided into subsets for each of the plurality of dilating mechanisms 1, or alternatively a single motor 131, crankshaft 134, or similar device could be coupled with a gearbox in order to engage the plurality of dilating mechanisms 1. Operation of the plurality of dilating mechanisms 1 can be as simple as pressing a button or flipping a switch, as previously described, in order to complete a circuit and engage the motor 131. In human-powered variations, a control such as the aforementioned handle 135 at the bottom of the present invention, can be used to engage the plurality of dilating mechanisms 1.

In one embodiment, the present invention further comprises an articulated pillar 4, an anchor 5, and a cord 6. The cord 6 is used to engage the articulated pillar 4 with the anchor 5; by adjusting tension in the cord 6, the articulated pillar 4 can be pulled towards the anchor 5. This allows a bend to be imparted to the present invention, enabling a user to switch the present invention between a straight configuration and a bent configuration. The articulated pillar 4 is connected normal to the base 2, standing straight up. The anchor 5 is mounted to the base 2 offset above the base 2 and next to the articulated pillar 4. This allows for the cord 6 to couple the articulated pillar 4 to the anchor 5 without interfering with operation of the plurality of dilating mechanisms 1. A first end 61 of the cord 6 is coupled to the anchor 5 while a second end 62 of the cord 6 is connected to a free end 41 of the articulated pillar 4. This potential embodiment is shown via FIG. 9-FIG. 14.

In a simplest embodiment, the articulated pillar 4 comprises a rigid segment 42 and an adjustable segment 43. The rigid segment 42, being the portion where the articulated pillar 4 is connected to the base 2, is positioned adjacent to the base 2. The adjustable segment 43 is adjacent to the rigid segment 42, at an end of the rigid segment 42 which is opposite the base 2. More specifically, the adjustable segment 43 is positioned next to a top end of the rigid segment 42 while a bottom end of the rigid segment 42 is positioned next to the base. The adjustable segment 43 is hingedly connected to the rigid segment 42 in order to allow the adjustable segment 43 to rotated about the top end of the rigid segment 42. Thus, by adjusting tension in the cord 6, the adjustable segment 43 can be pulled downwards to create a bend in the present invention. When tension in the cord 6 is reduced, the articulated pillar 4 can return to an equilibrium linear (e.g. vertical) position, with the adjustable segment 43 rotating upwards to be collinear with the rigid segment 42.

Describing this connection in more detail, an auxiliary drive mechanism 51 is provided in conjunction with the anchor 5. The anchor 5 itself is preferably a spool 52; by rotating the spool 52 the cord 6 can be tightened or loosened. The auxiliary drive mechanism 51 is able to cause rotation thanks to being torsionally coupled to the spool 52. Describing the engagement between the cord 6 and the anchor 5, the first end 61 of the cord 6 is wound about the spool 52 in order to enable adjustment of tension in the cord 6 through rotation of the spool 52. As the spool 52 tightens the cord 6, the second end 62 pulls on the adjustable segment 43 in order to create a bend in the present invention.

Figure 11:
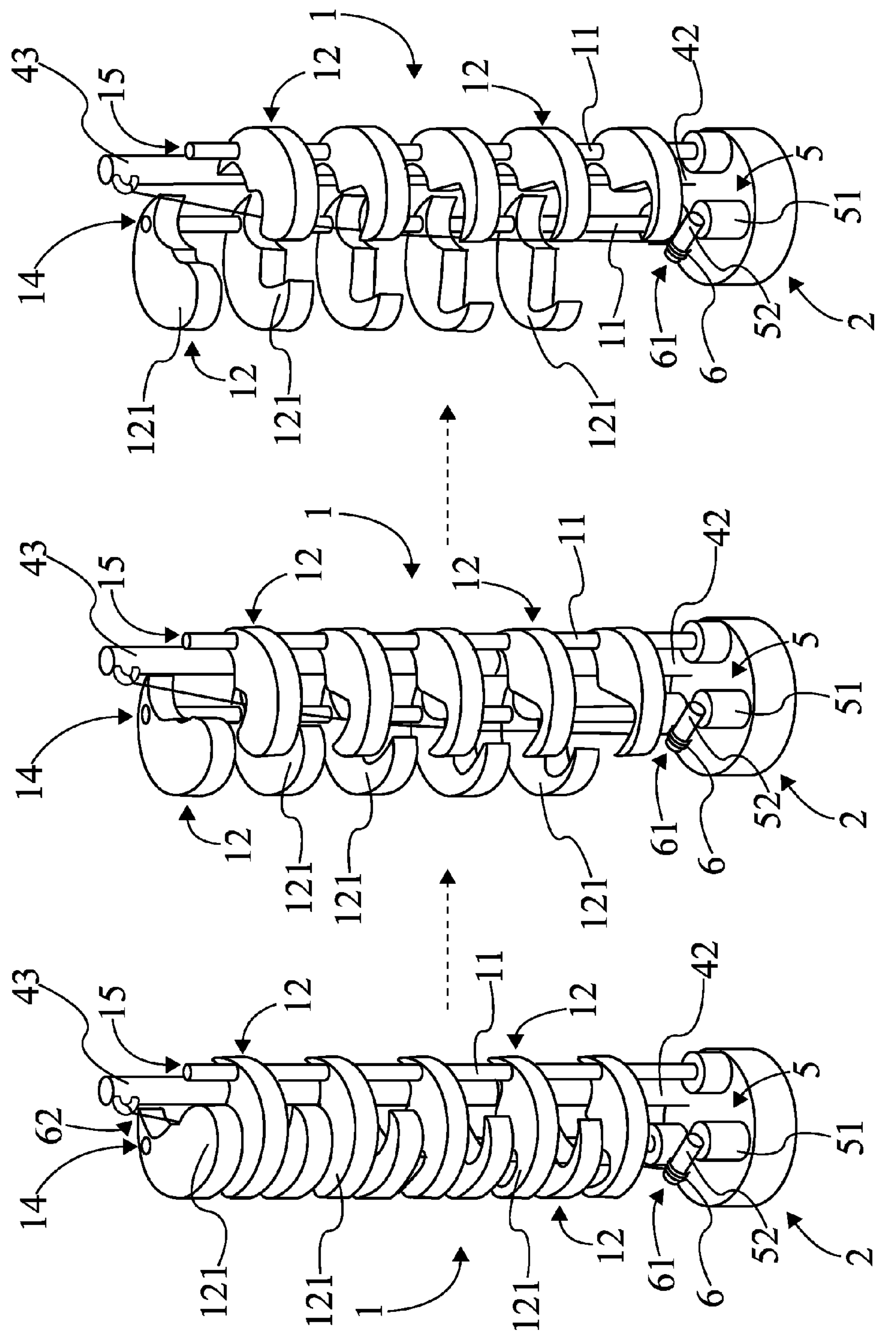
FIG. 11 is a perspective view showing the bendable embodiment of the present invention transitioning from the contracted configuration to the expanded configuration.
Figure 12:
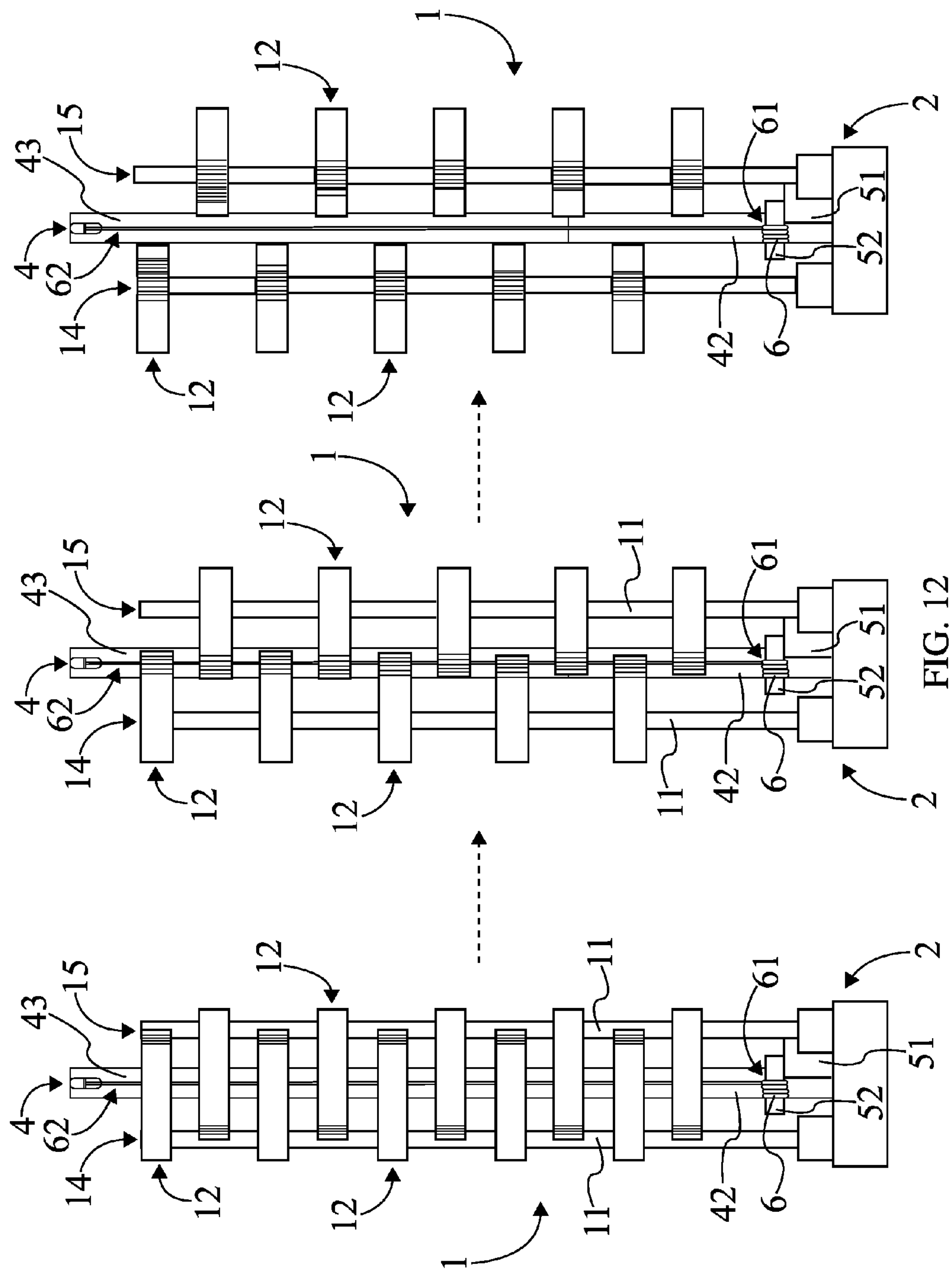
FIG. 12 is a front view showing the bendable embodiment of the present invention transitioning from the contracted configuration to the expanded configuration.
Figure 13:
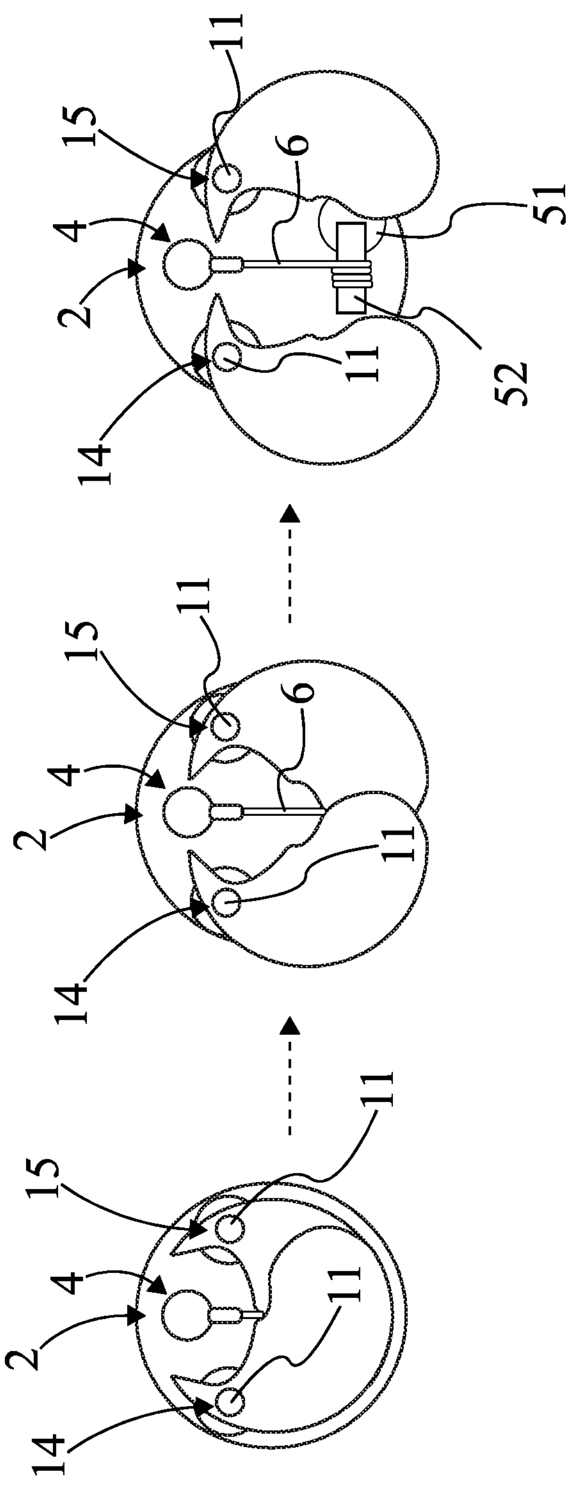
FIG. 13 is a top view showing the bendable embodiment of the present invention transitioning from the contracted configuration to the expanded configuration.
Figure 14:
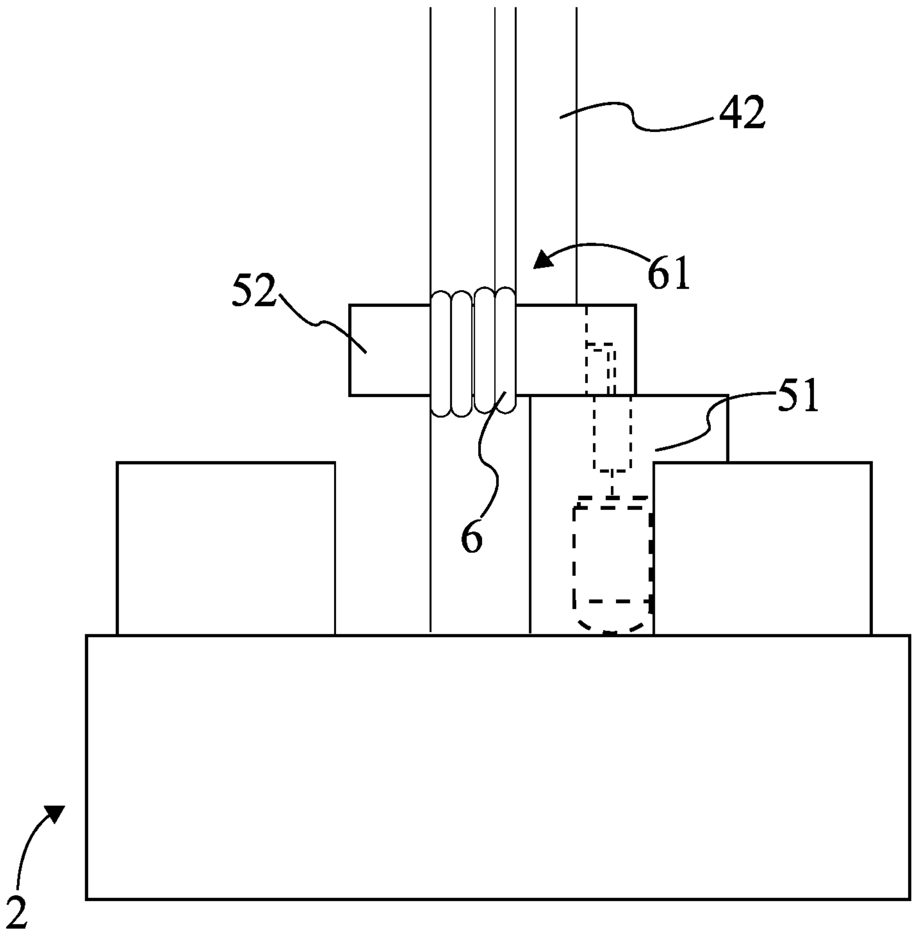
FIG. 14 is an enhanced front view showing a potential embodiment for an auxiliary drive mechanism for the bendable configuration.
Figure 15:
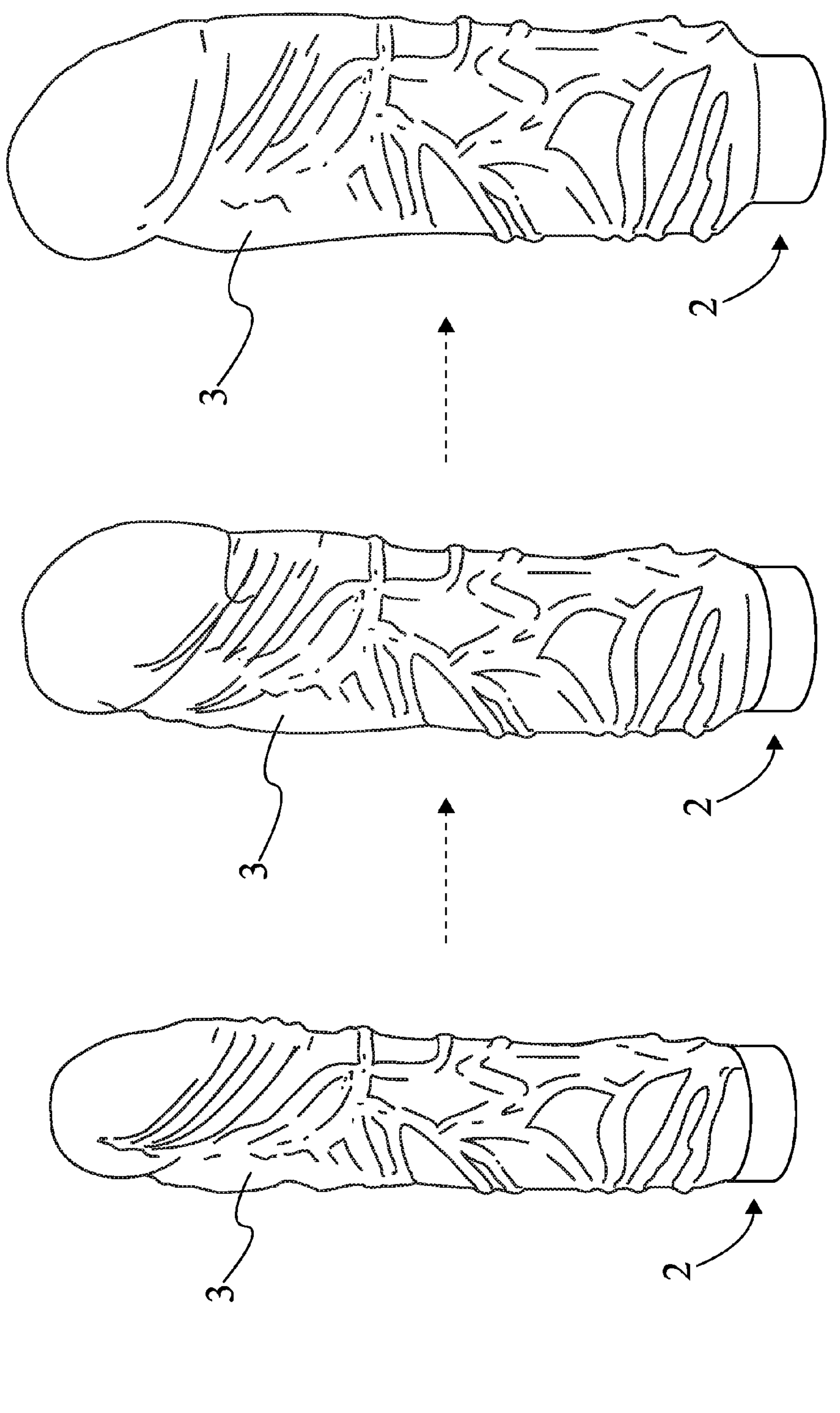
FIG. 15 is a perspective view showing the present invention, including elastic membrane, transitioning from the contracted configuration to the expanded configuration.

Preferably, in order to ensure that the cord 6 does not become tangled with the lobes 121 in a contracted configuration, each of the lobes 121 comprises a slit. This slit provides a space for the cord 6 to travel through without contacting the lobe 121. Such a slit is desirable as contact with a lobe 121 could affect tension in the cord 6 and cause the present invention to unintentionally bend. This is most clearly shown in the expanded configuration as shown in FIG. 11.

The auxiliary drive mechanism 51, as with the primary drive mechanism 13 for each of the plurality of dilating mechanisms 1, can be motorized or human-powered. To allow for the auxiliary drive mechanism 51 to be operating without requiring removal of the elastic membrane 3, an auxiliary drive control is preferably mounted adjacently mounted to the base 2. Whether a switch (for a motorized drive) or a handle 135 (for a human-powered drive), the auxiliary drive control can be used to engage or disengage the auxiliary drive mechanism 51 in order to bend or unbend the present invention.

It is noted that while the articulated pillar 4 has been described as having two segments (i.e. the rigid segment 42 and the adjustable segment 43), any number of hinged segments can be provided to allow for a finer adjustment of the bend of the present invention. A further possibility it the integration of the articulated pillar 4 into the primary shaft 11 for each of the plurality of dilating mechanisms 1. This more complicated embodiment would require that each primary shaft 11 not only be rotatable but also be bendable.

In a simpler variation of the above embodiment, a simple fixed pillar is provided in place of the articulated pillar 4, anchor 5, and cord 6. The fixed pillar is not adjustable nor does it enable bending of the present invention; instead it serves as a structural support to increase firmness and durability of the present invention. Other enhancements are possible while remaining within the scope of the present invention. For example, a dome-shaped cap can be connected atop the articulated pillar 4 or the plurality of dilating mechanisms 1 to help create a more phallic appearance and feel. Similarly, a vibrator mechanism could be installed within the present invention to provide enhanced functionality. These are just a few examples of possibilities that can be incorporated into the present invention.

Although the invention has been explained in relation to its preferred embodiment, it is to be understood that many other possible modifications and variations can be made without departing from the spirit and scope of the invention as hereinafter claimed.

What is claimed is:

1. A radially adjustable sex toy:

a plurality of dilating mechanisms;

a base;

an elastic membrane;

a drive mechanism;

each of the plurality of dilating mechanisms comprises a primary shaft and a plurality of lateral bracing members;

the primary shaft of each of the plurality of dilating mechanisms being peripherally distributed about the base;

the primary shaft being rotatably connected into the base;

each of the plurality of lateral bracing members being connected adjacent and perpendicular to the primary shaft;

the plurality of lateral bracing members being distributed along the primary shaft;

the drive mechanism being housed in the base;

the primary shaft of each of the plurality of dilating mechanisms being torsionally coupled to the drive mechanism; and the primary shaft and the plurality of lateral bracing members being sleeved by the elastic membrane.

2. The radially adjustable sex toy as claimed in claim 1 comprises:

each of the plurality of lateral bracing members comprises a lobe;

the base being elliptical; and the lobe being perimetrically aligned with the base in a contracted configuration.

3. The radially adjustable sex toy as claimed in claim 1 comprises:

the plurality of dilating mechanisms comprises a first dilating mechanism and a second dilating mechanism;

the first dilating mechanism being positioned opposite the second dilating mechanism along a chord of the base;

the plurality of lateral bracing members of the first dilating mechanism being axially offset from the plurality of lateral bracing members of the second dilating mechanism; and the plurality of lateral bracing members of the first dilating mechanism being interspersed between the plurality of lateral bracing members from the second dilating mechanism.

4. The radially adjustable sex toy as claimed in claim 1 comprises:

the drive mechanism comprises an at least one motor and a power input;

the at least one motor being housed in the base;

the power input traversing into the base;

the power input being electrically connected to the at least one motor; and an output of the at least one motor being torsionally coupled to the primary shaft of at least one of the plurality of dilating mechanisms.

5. The radially adjustable sex toy as claimed in claim 1 comprises:

the drive mechanism comprises an at least one motor and a battery;

the at least one motor being housed in the base;

the battery being housed in the base;

the battery being electrically connected to the at least one motor; and an output of the at least one motor being torsionally coupled to the primary shaft of at least one of the plurality of dilating mechanisms.

6. The radially adjustable sex toy as claimed in claim 1 comprises:

the drive mechanism comprises an at least one crankshaft and an at least one handle;

the at least one crankshaft being rotatably mounted into the base;

the at least one crankshaft being axially and adjacently connected to the primary shaft of at least one of the plurality of dilating mechanisms;

the at least one handle being positioned adjacent to the base; and the at least one handle being adjacently connected to the at least one crankshaft.

7. The radially adjustable sex toy as claimed in claim 1 comprises:

an articulated pillar;

an anchor;

a cord;

the articulated pillar being connected normal to the base;

the anchor being mounted to the base, adjacent to the articulated pillar and offset from the base;

a first end of the cord being coupled with the anchor; and a second end of the cord being connected to a free end of the articulated pillar.

8. The radially adjustable sex toy as claimed in claim 7 comprises:

the articulated pillar comprises a rigid segment and an adjustable segment;

the rigid segment being positioned adjacent to the base; and the adjustable segment being positioned adjacent to the rigid segment, opposite the base.

9. The radially adjustable sex toy as claimed in claim 7 comprises:

an auxiliary drive mechanism;

the anchor being a spool;

the first end of the cord being wound about the spool; and the auxiliary drive mechanism being torsionally coupled to the spool.

* * * * *